United States Patent
O'Connor et al.

(10) Patent No.: US 7,983,022 B2
(45) Date of Patent: Jul. 19, 2011

(54) ELECTRICALLY CONNECTING MULTIPLE CATHODES IN A CASE NEGATIVE MULTI-ANODE CAPACITOR

(75) Inventors: Laurie M. O'Connor, East Aurora, NY (US); Kenneth B. Talamine, Amherst, NY (US); Keith W. Seitz, Clarence Center, NY (US); Steven Schmidt, Blaine, MN (US); Anthony Perez, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 248 days.

(21) Appl. No.: 12/397,779

(22) Filed: Mar. 4, 2009

(65) Prior Publication Data

US 2010/0134955 A1   Jun. 3, 2010

Related U.S. Application Data

(60) Provisional application No. 61/033,816, filed on Mar. 5, 2008.

(51) Int. Cl.
*H01G 9/04* (2006.01)

(52) U.S. Cl. ........ 361/508; 361/509; 361/516; 361/517; 361/519; 361/540

(58) Field of Classification Search .......... 361/503–504, 361/508, 509, 511–512, 516–519, 523–529, 361/540–541
See application file for complete search history.

(56) References Cited

U.S. PATENT DOCUMENTS

| | | | |
|---|---|---|---|
| 5,926,362 A * | 7/1999 | Muffoletto et al. | ........... 361/503 |
| 6,388,866 B1 | 5/2002 | Rorvick et al. | |
| 6,402,793 B1 | 6/2002 | Miltich et al. | |
| 6,477,037 B1 | 11/2002 | Nielsen et al. | |
| 6,560,089 B2 | 5/2003 | Miltich et al. | |
| 6,586,134 B2 | 7/2003 | Skoumpris | |
| 6,603,654 B2 | 8/2003 | Rorvick et al. | |
| 6,648,928 B2 | 11/2003 | Nielsen et al. | |
| 6,807,048 B1 | 10/2004 | Nielsen et al. | |

(Continued)

FOREIGN PATENT DOCUMENTS

EP   1431990 A2   6/2004

(Continued)

OTHER PUBLICATIONS

European Search Report, Application Serial No. 09154460.1, dated Jul. 7, 2009.

*Primary Examiner* — Nguyen T Ha
(74) *Attorney, Agent, or Firm* — Michael F. Scalise

(57) ABSTRACT

A capacitor is described. The capacitor includes a casing of first and second casing members secured to each other to provide an enclosure, a feedthrough electrically insulated from the casing and extending there from through a glass-to-metal seal, first and second anodes electrically connected to each other within the casing, a cathode, and an electrolyte. The cathode is of a cathode active material deposited on planar faces of the first and second casing members. There is also a cathode current collector disposed intermediate the first and second anodes. The cathode current collector supports cathode active material on both of its major faces and includes a tab that is directly electrically connected to a ferrule of the glass-to-metal seal. That way, the casing is the negative terminal for the cathode and a feedthrough pin extending through the glass-to-metal seal is the positive terminal for the anode of the capacitor.

21 Claims, 12 Drawing Sheets

U.S. PATENT DOCUMENTS

| | | | |
|---|---|---|---|
| 6,819,544 B1 | 11/2004 | Nielsen et al. | |
| 6,850,405 B1 * | 2/2005 | Mileham et al. | 361/302 |
| 6,999,304 B2 | 2/2006 | Schmidt et al. | |
| 7,006,347 B1 * | 2/2006 | Kroll et al. | 361/503 |
| 7,085,126 B2 * | 8/2006 | Muffoletto et al. | 361/517 |
| 7,271,994 B2 * | 9/2007 | Stemen et al. | 361/508 |
| 7,483,260 B2 * | 1/2009 | Ziarniak et al. | 361/541 |
| 7,715,174 B1 * | 5/2010 | Beauvais et al. | 361/528 |
| 2003/0072124 A1 | 4/2003 | O'Phelan et al. | |
| 2005/0052825 A1 | 3/2005 | O'Phelan | |
| 2006/0012942 A1 | 1/2006 | Poplett | |
| 2006/0012943 A1 | 1/2006 | Sherwood | |
| 2006/0012945 A1 | 1/2006 | Doffing et al. | |

FOREIGN PATENT DOCUMENTS

EP  1936643 A1  6/2008

\* cited by examiner

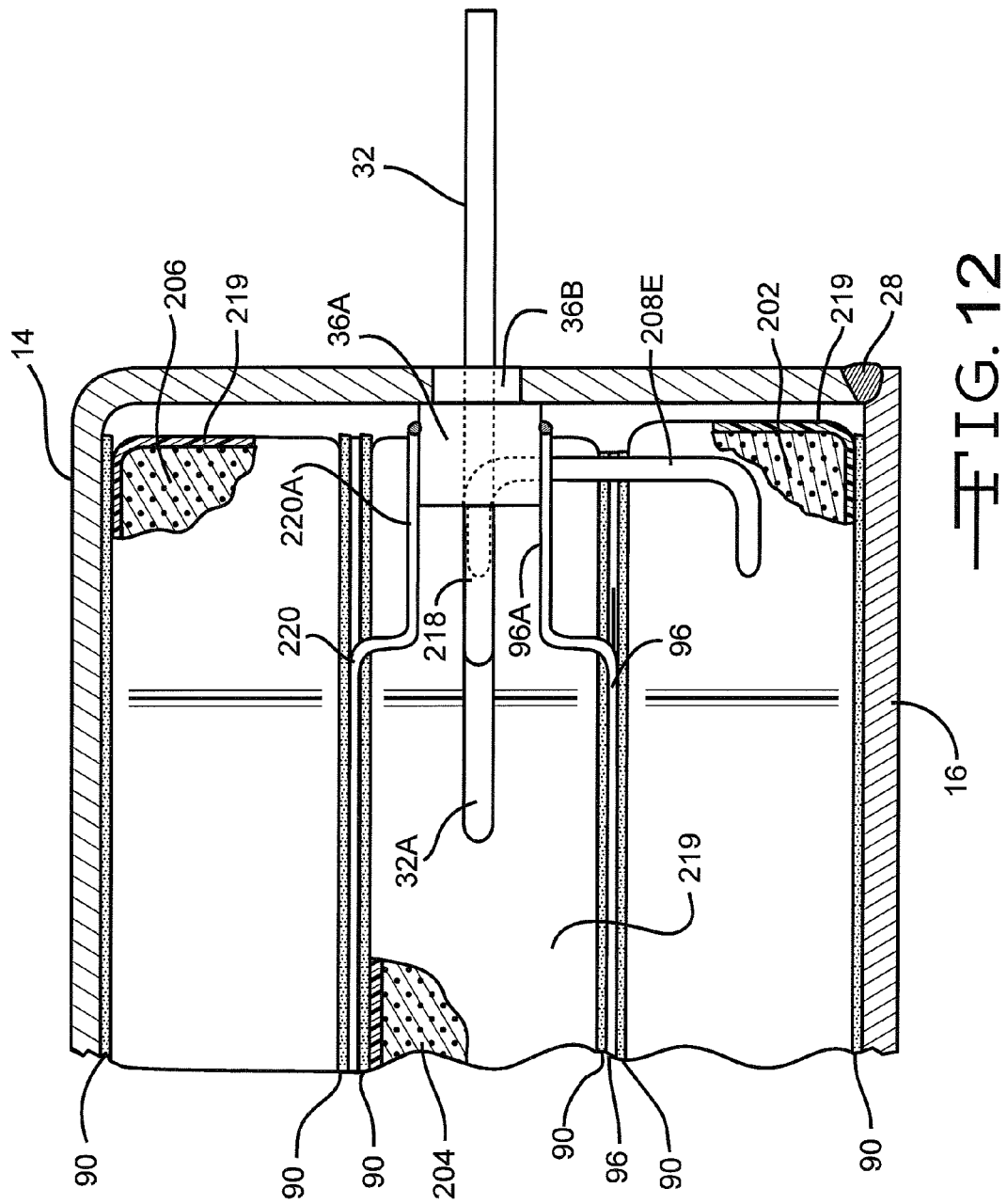

ELECTRICALLY CONNECTING MULTIPLE CATHODES IN A CASE NEGATIVE MULTI-ANODE CAPACITOR

CROSS-REFERENCE TO RELATED APPLICATION

This application claims priority from U.S. Provisional Application Ser. No. 61/033,816, filed Mar. 5, 2008.

BACKGROUND OF THE INVENTION

1. Field of the Invention

The present invention generally relates to a capacitor and, more particularly, to a capacitor containing at least two anodes and an intermediate cathode. The anodes are connected to a common terminal that is electrically isolated from the capacitor casing to which the cathode is electrically connected.

2. Description of Related Art

As more and more medical applications are investigated and implemented to aid and assist the human body, devices needed to deliver the desired therapy are becoming increasingly more sophisticated, both functionally and in terms of their structural makeup. Modern implantable devices require power sources that are smaller in size, but powerful enough to meet the therapy requirements. For example, a cardiac defibrillator has a battery powering circuits performing such functions as, for example, the heart sensing and pacing functions. This requires electrical current of about 1 microampere to about 100 milliamperes. From time-to-time, the cardiac defibrillator may require a generally high rate, pulse discharge load component that occurs, for example, during charging of a capacitor assembly in the defibrillator for the purpose of delivering an electrical shock to the heart to treat tachyarrhythmias, the irregular, rapid heartbeats that can be fatal if left uncorrected. This requires electrical current of about 1 ampere to about 4 amperes.

The current trend in medicine is to make cardiac defibrillators, and like implantable devices, as small and lightweight as possible without compromising their power. This, in turn, means that capacitors contained in these devices must be readily adaptable in how they are connected to each other as well as to the battery and the device circuitry. In that light, a number of patents and publications disclose electrical energy storage devices including capacitors having a dual anode structure.

One is described in U.S. Pat. No. 7,483,260 to Ziarniak et al., which is assigned to the assignee of the present invention and incorporated herein by reference. This patent relates to a design that provides first and second anodes electrically connected to each other within the casing, a cathode, and a working electrolyte. The anodes are electrically connected in parallel by an anode wire extending between them. A feedthrough wire extending outside the casing and electrically isolated therefrom is electrically connected to this anode wire intermediate the first and second anodes. The cathode is disposed between the first and second anodes and includes a tab extending from the cathode current collector. The cathode current collector tab is then tack welded to the inside surface of a casing side wall to electrically connect the cathode to the casing. The casing member to which the cathode current collector tab is tack welded is then secured to a second casing member to provide a hermetically sealed casing.

While the Ziarniak et al. capacitor construction is completely acceptable, there is a need for greater flexibility in capacitor designs. This is driven, in part, by the myriad of applications described above. Instead of electrically connecting the cathode current collector tab to an internal location of the casing sidewall, the present design has the cathode tab electrically connected directly to the ferrule of the glass-to-metal seal (GTMS). Connecting the cathode current collector tab to the GTMS provides the designer with another option when building capacitors for a particular need that may not have been entirely met by the Ziarniak et al. design.

SUMMARY OF THE INVENTION

Accordingly, embodiments of the present invention are provided that meet at least one or more of the following objects:

According to the present invention, therefore, a capacitor is provided comprising a casing of first and second casing members, a feedthrough wire or pin electrically insulated from the casing and extending to the outside thereof, first and second anodes, an intermediate cathode, and a working electrolyte. The first casing member has a first face wall joined to a surrounding side wall, and the second casing member comprises a second face wall in the form of a plate. The casing is formed by joining the second plate to the first surrounding sidewall.

The first anode is housed within the casing and comprises a first pellet of anode active material comprising inner and outer major face walls and including a first wire extending therefrom and electrically connected within the casing to the feedthrough. The second anode is also housed within the casing and comprises a second pellet of anode active material comprising inner and outer major face walls and including a second wire extending there from and electrically connected within the casing to the first pellet of anode active material. Preferably a proximal end of the first and second wires is embedded in the respective anode pellets.

The cathode comprises cathode active material supported by and in contact with the first face wall of the first casing member and the face wall of the second casing plate. A first cathode current collector is disposed between or intermediate the first and second anodes. The first cathode current collector has opposed first and second major faces supporting cathode active material and positioned opposite the inner major faces of the respective first and second anode pellets. A tab extending from the cathode current collector is directly electrically connected to the ferrule of a glass-to-metal seal (GTMS). The GTMS electrically insulates the feedthrough wire from the casing. That way, the casing/ferrule is the negative terminal for the cathode.

A working electrolyte contacts the cathode active material and the first and second anodes.

Within the capacitor casing, the second anode wire is electrically connected to the feedthrough pin. This serves to directly connect both anode pellets to the feedthrough pin in a serial manner. The second anode wire may be a separate structure from the first anode wire although each is in continuity with the feedthrough pin through the serial anodes. Alternatively, the anode wires are a continuous structure embedded in the first and second pellets and connected to the feedthrough pin. For this latter embodiment, the anode pellets are connected to the feedthrough pin in parallel. In another embodiment in which the anode pellets are connected to the feedthrough pin in series, the second anode wire is not connected to the feedthrough pin or to the first anode wire. Instead, it is connected only to the first anode pellet.

The capacitor may further comprise a first separator enclosing the first anode pellet and a second separator enclosing the second anode pellet. The separators may be formed as pouches that enclose the anode pellets. In a further embodiment, the first anode wire extending from the first anode pellet, the second anode wire extending from the second anode pellet, and at least a portion of the GTMS are enclosed in a molded polymeric material.

The capacitor of the present invention is not limited solely to a dual anode structure. The capacitor may comprise additional anodes and cathode current collectors supporting cathode active material on the major faces thereof. For example, in a three anode configuration, a third pellet of anode active material includes a third anode wire extending therefrom and electrically connected within the casing to the second anode pellet. A second cathode current collector is disposed between the second and third anode pellets. The second cathode current collector has opposed first and second major faces provided with cathode active material and positioned opposite the inner major faces of the respective second and third anode pellets. The second cathode current collector has a second tab that can be directly connected to the casing, the first cathode current collector tab or the ferrule. This introduces a greater degree of flexibility to the capacitor design.

Also according to the present invention, a method for making a capacitor comprises the steps of providing a casing comprising first and second casing members. Each of casing members include a face wall supporting and in contact with a cathode active material. An anode assembly comprises a first anode pellet of anode active material including a first anode wire extending therefrom and electrically connected to a feedthrough. A second anode comprises a second pellet of anode active material including a second anode wire extending therefrom and electrically connected to the first anode pellet. A cathode current collector having opposed first and second major faces provided with cathode active material is disposed between the inner major faces of the first and second anode pellets. A tab extending from the cathode current collector is connected to the ferrule of the GTMS. This forms an anode/cathode assembly that is positioned inside the first casing member with the feedthrough pin electrically connected to the anode pellets extending out of the casing through the GTMS so that it is electrically isolated from the casing/ferrule electrically connected to the cathode. The first casing member is hermetically secured to the second casing member to provide an enclosure containing the anode/cathode assembly. Finally, a working electrolyte is provided inside the casing to operatively associate the cathode with the first and second anode pellets. The step of electrically connecting the cathode current collector to the ferrule of the GTMS may be performed by spot welding the current collector tab to the ferrule, preferably by laser welding.

The method may further include the step of enclosing each of the first and second anode pellets within a separator. The method may further include the step of placing the anode assembly in a mold interior and injecting a polymeric material into the mold to enclose and immobilize a major portion of the feedthrough including the cathode current collector welded to the feedthrough ferrule and the adjacent anodes.

The foregoing and additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which:

FIG. 12 is a cross-sectional view similar to that of FIG. 9 except for a three anode/two cathode current collector assembly.

The present invention will be described in connection with preferred embodiments, however, it will be understood that there is no intent to limit the invention to the embodiments described. On the contrary, the intent is to cover all alternatives, modifications, and equivalents as may be included within the scope of the invention as defined by the appended claims.

DETAILED DESCRIPTION OF THE PREFERRED EMBODIMENTS

Figure 1:
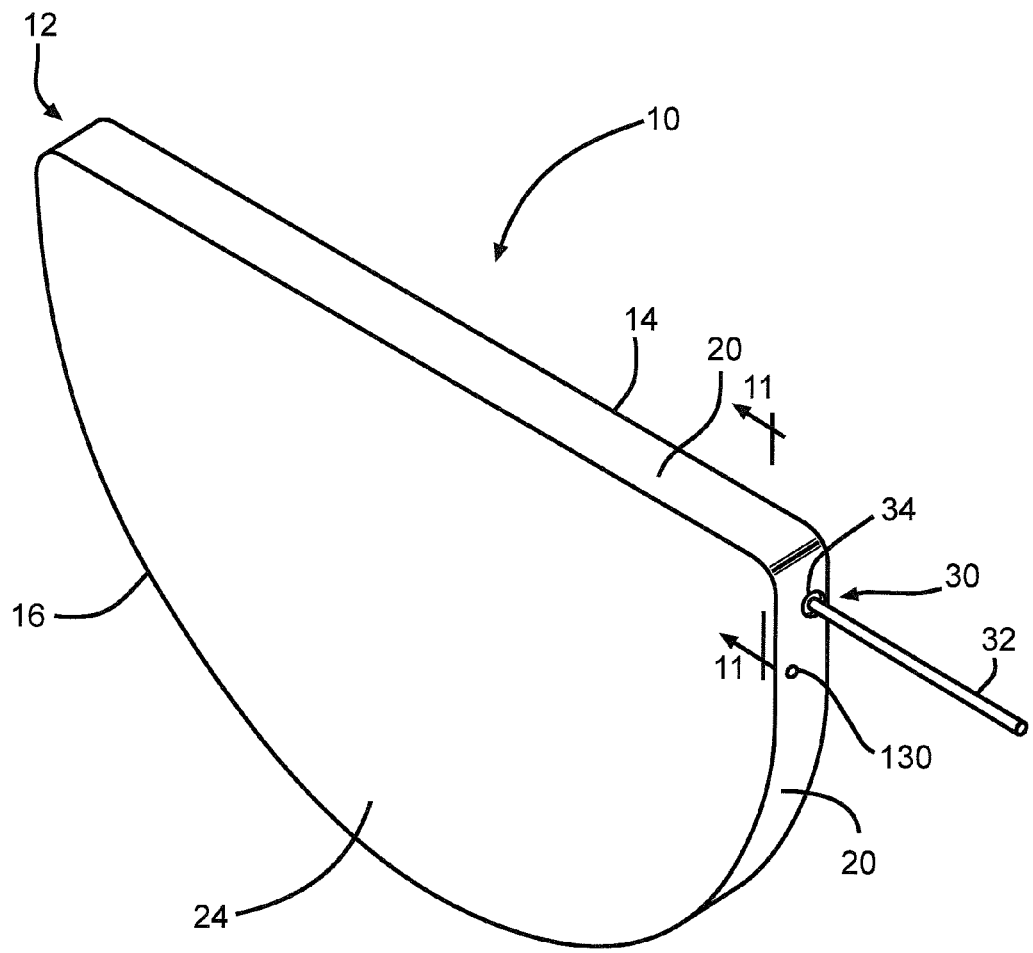
FIG. 1 is a perspective view of a capacitor 10 according to the present invention.

Turning now to the drawings, FIG. 1 is a perspective view of a capacitor according to the present invention. The capacitor 10 comprises at least two anodes of an anode active material and a cathode of a cathode active material housed inside a hermetically sealed casing 12. The capacitor electrodes are operatively associated with each other by a working electrolyte (not shown) contained inside the casing. The anodes, cathode and electrolyte of capacitor 10 will be described in detail hereinafter.

Figure 9:
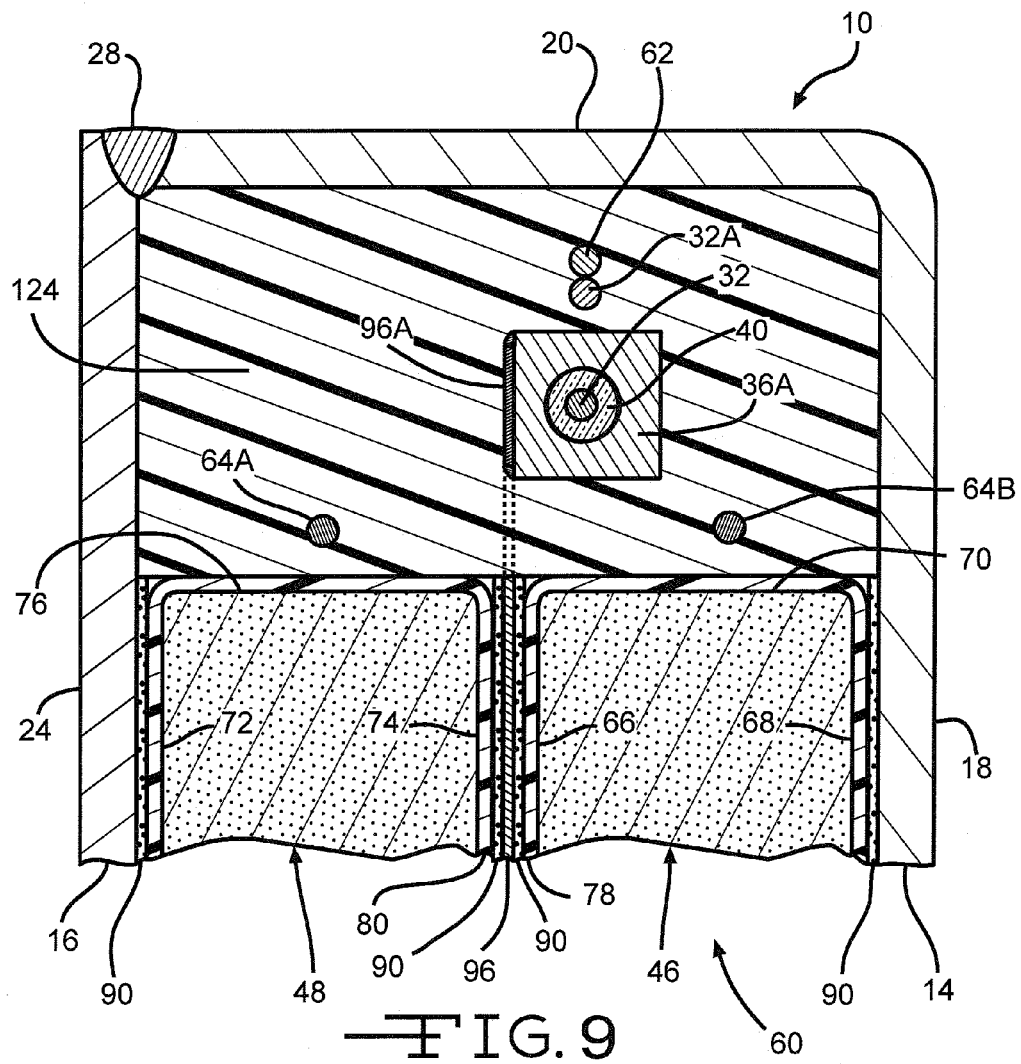
FIG. 9 is a cross sectional view taken along line 9-9 of FIG. 1.
Figure 10:
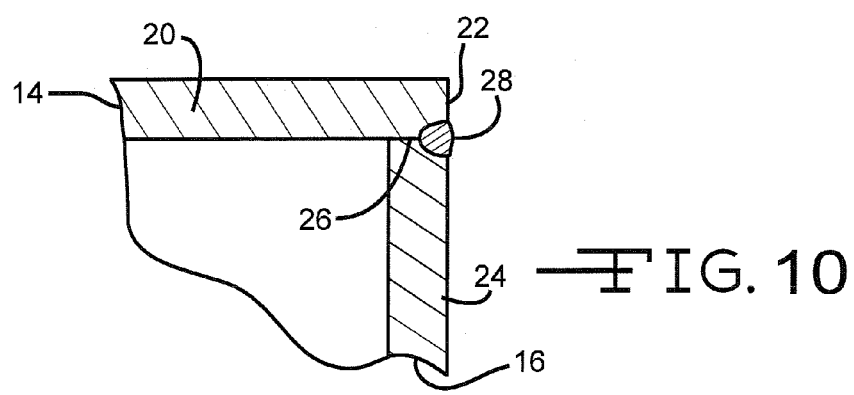
FIG. 10 is a cross sectional view of the cover-to-casing seal of the enclosure of the capacitor 10 of FIG. 1.

As particularly shown in FIGS. 1, 9 and 10, the casing 12 is of metal material comprising first and second casing members 14 and 16. First casing member 14 comprises a first face wall 18 joined to a surrounding side wall 20 extending to an edge 22. Second casing member 16 is in the shape of a plate and comprises a second face wall 24 having a surrounding edge 26. The casing members 14 and 16 are hermetically sealed together by welding the overlapping edges 22 and 26 where they contact each other. The weld 28 is provided by any conventional means; however, a preferred method is by laser welding.

Figure 2:
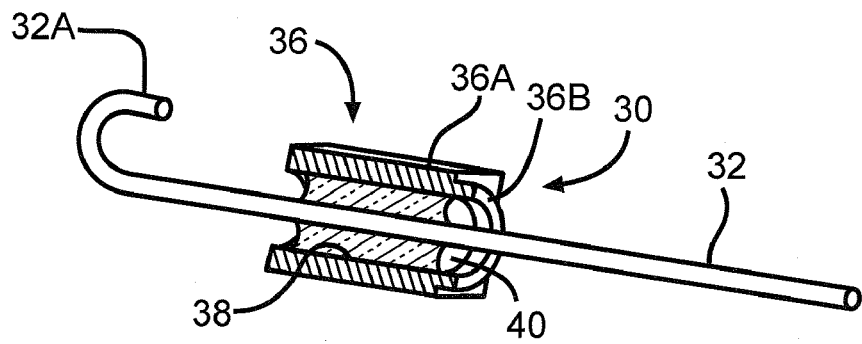
FIG. 2 is a cross-sectional perspective view of one embodiment of a feedthrough 30 used in the capacitor 10.

FIG. 2 is a cross-sectional perspective view of a feedthrough 30 that electrically insulates an anode terminal wire 32 from the casing 12. The terminal wire 32 extends from within the casing 12 to the outside thereof. The location of a hole 34 in the surrounding side wall 20 of the casing member 14 into which the feedthrough 30 is mounted is preferably offset towards the front edge 22 or towards the face wall 18 in order to align with an embedded wire of one of the anodes, as will be described subsequently.

Feedthrough 30 is a glass to metal seal (GTMS) comprising a ferrule 36 defining an internal cylindrical through bore or passage 38 of constant inside diameter. The ferrule 36 comprises a proximal portion 36A having a rectangular cross-section and a distal portion 36B having a cylindrical cross-section. As will be described in detail hereinafter, the proximal portion 36A is preferably provided with its rectangular shape so that the cathode current collector can be directly welded thereto. In that respect, the proximal portion 36A may have a partially cylindrical shape with a planar side for connection to the cathode current collector. Alternatively, the ferrule may have a rectangular cross-section along its entire length instead of the illustrated cylindrically shaped distal portion 36B. An insulative glass 40 provides a hermetic seal between the bore 38 and the anode terminal wire 32 passing therethrough. The terminal wire 32 has a J-shaped interior portion 32A for connection to one or more anode wires within casing 12. The glass 40 is, for example, ELAN® type 88 or MANSOL™ type 88.

Figure 3:
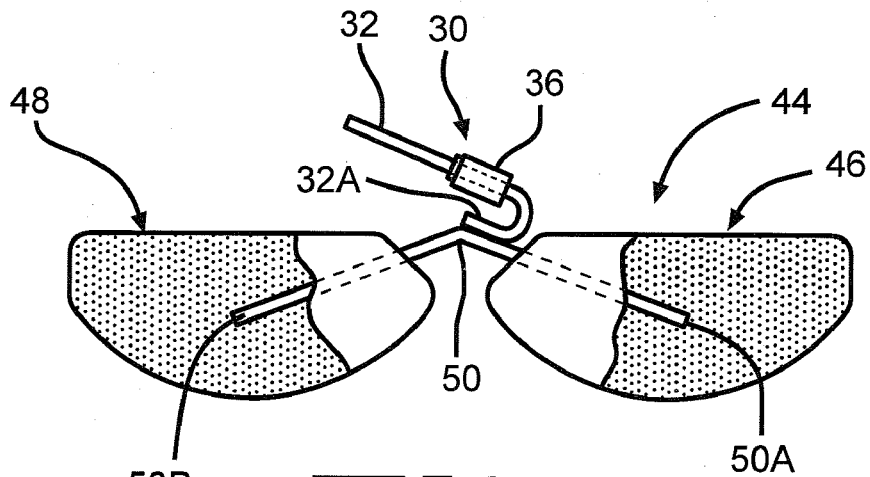
FIGS. 3 and 3A are side elevation views of respective anode assemblies 44 and 44A comprising a pair of anode pellets 46 and 48 connected in parallel to a feedthrough 30.

Capacitor 10 further comprises two or more anodes that are connectable to the terminal wire 32 of feedthrough 30 within the casing 12. FIG. 3 is a side elevation view of an anode assembly 44 comprising a pair of anodes connected in parallel to the terminal wire 32. The anode assembly 44 includes a first anode pellet 46 and a second anode pellet 48. An anode wire 50 has a first end portion 50A embedded in the first pellet 46 and a second end portion 50B embedded in the second pellet 48. The wire 50 is a continuous member that will be electrically connected to the J-shaped interior portion 32A of the anode terminal wire 32 by a suitable joining process, such as laser welding, in a later manufacturing step.

Figure 3A:
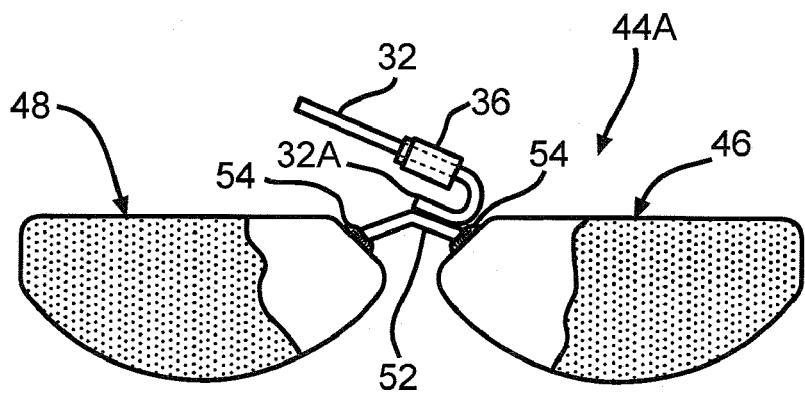

In another embodiment of an anode assembly 44A shown in FIG. 3A, portions of an anode wire 52 are not embedded in the anode pellets 46, 48. Instead, opposed distal ends of the wire 52 are connected to surrounding edges of the respective pellets 46, 48, such as by welds 54. However, the first and second anode pellets 46, 48 are still connected to the terminal wire 32 in parallel.

Figure 3B:
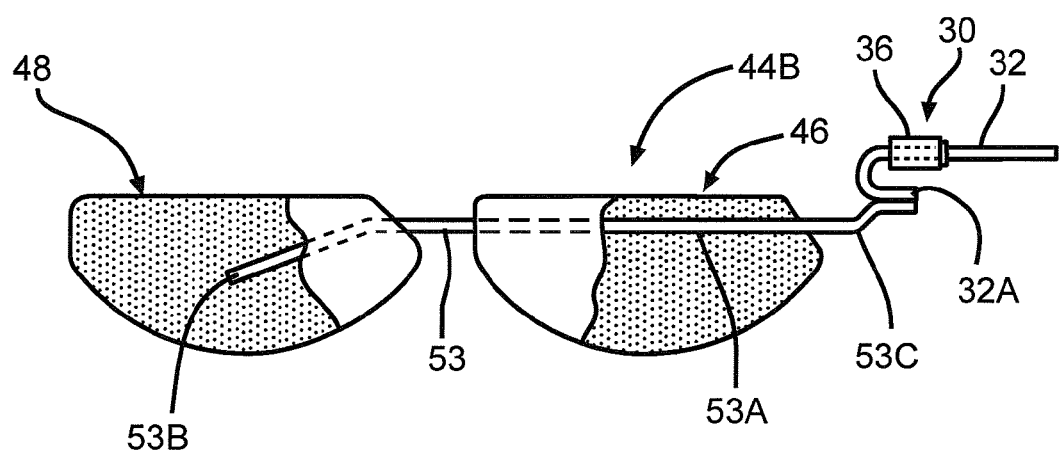
FIG. 3B is a side elevation view of an anode assembly 44B comprising the pair of anode pellets 46, 48 connected in series to the feedthrough 30.
Figure 4:
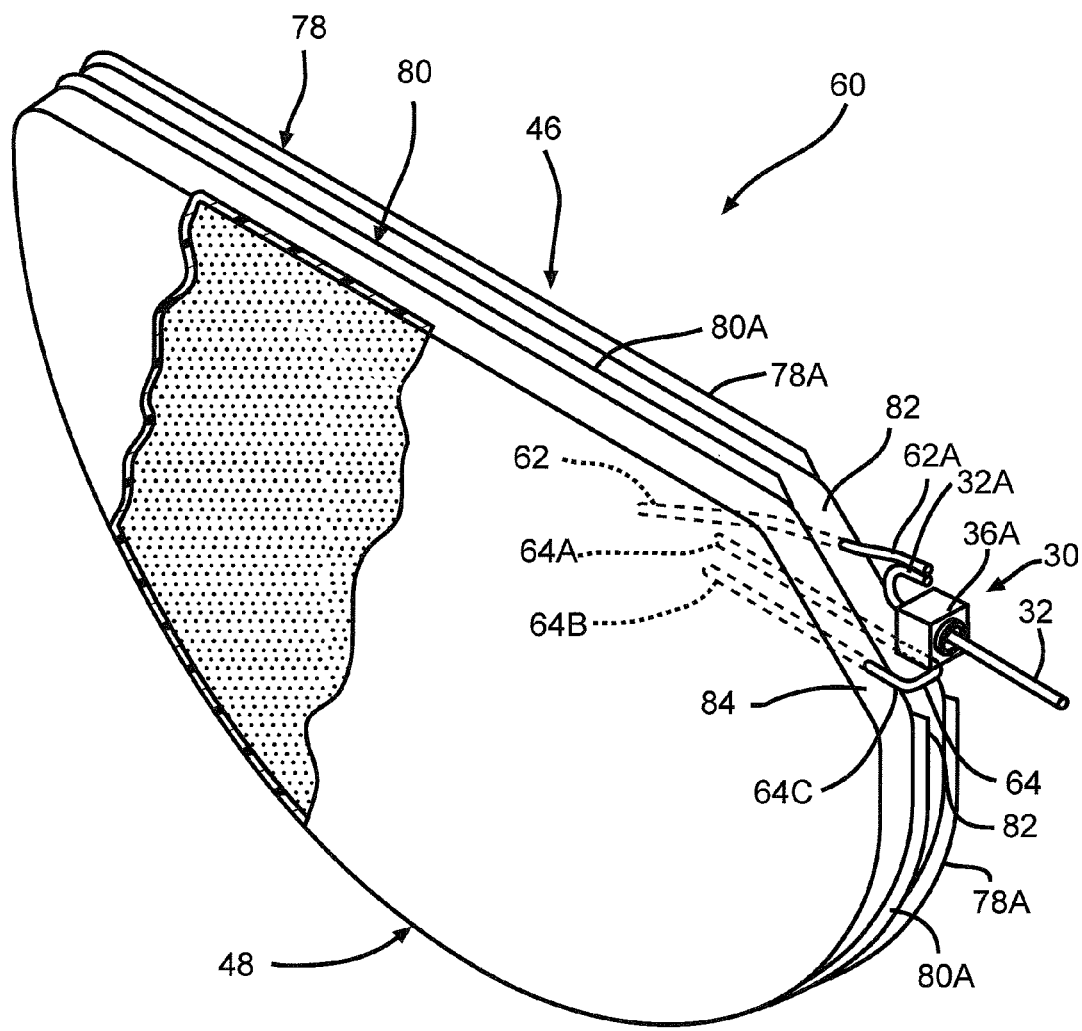
FIG. 4 is a perspective view of a dual anode assembly 60 according to the present invention prior to a cathode being fitted between the anode pellets 46 and 48.

Another embodiment of an anode assembly 44B shown in FIG. 3B has the pair of anode pellets 46, 48 connected in series to the terminal wire 32. The anode assembly 44B includes an anode wire 53 having a first end portion 53A embedded in and extending completely through the first pellet 46 to a second end portion 53B and a third end portion 53C. The second end portion 53B is embedded in the second pellet 48. The third end portion 53C of the anode wire extending from the first anode pellet 46 opposite the second pellet 48 is connected to the J-shaped interior portion 32A of the anode terminal wire 32. This is preferably done by laser welding.

Referring to FIGS. 4 to 9, another embodiment of a dual anode assembly 60 according to the present invention is depicted therein. In this anode assembly 60, a first wire 62 partially embedded in the first anode pellet 46 has a distal portion 62A electrically connected to the J-shaped interior portion 32A of the terminal wire 32. In a similar manner as the assembly previously illustrated in FIG. 3, a second bridging wire 64 has an end portion 64A embedded in the first pellet 46 and a second end portion 64B embedded in the second pellet 48. The wire 64 has an exposed portion 64C that is not directly connected to the terminal wire 32 or to the first wire 62 of anode pellet 46. Instead, it connects directly to the first and second anode pellets 46, 48 and continuity to the embedded first wire 62 and ultimately the terminal wire 32 is through the active material of the first anode pellet 46. In this manner, the anode pellets 46 and 48 are connected to terminal wire 32 in series.

As particularly shown in FIG. 9, the first anode pellet 46 comprises an inner major face wall 66 and an outer major face wall 68, both extending to a surrounding edge 70. Similarly, the second anode pellet 48 comprises an inner major face wall 72 and an outer major face wall 74, both extending to a surrounding edge 76. The anode pellets 46, 48 are then folded at the bridging wire 64 so that their respective inner faces 66, 74 are adjacent to each other. This provides the anode bridging wire 64 with its exposed portion 64C intermediate the pellets 46, 48 having a generally U-shaped configuration.

The anode active material of the anode pellets 46, 48 is typically of a metal selected from the group consisting of tantalum, aluminum, titanium, niobium, zirconium, hafnium, tungsten, molybdenum, vanadium, silicon, germanium, and alloys and/or mixtures thereof in the form of a pellet. As is well known by those skilled in the art, the anode metal in powdered form, for example tantalum powder, is compressed into a pellet having the previously described anode wires embedded therein and extending therefrom. The anode pellets 46, 48 are sintered under a vacuum at high temperatures. The porous pellets 46, 48 are then anodized in a suitable electrolyte. This serves to form a continuous dielectric oxide film thereon. The anode assembly comprising the pellets 46, 48 and their associated anode wires is then formed to a desired voltage to produce an oxide layer over the sintered bodies and the anode wire. The anode can also be of an etched aluminum or titanium foil.

The capacitor 10 preferably comprises separators of electrically insulative material that completely surround and envelop the anodes. For example, the anode assembly 60 shown in FIG. 4 comprises a first separator 78 enclosing the first anode 46 and a second separator 80 enclosing the second anode 48. The separators 78, 80 may be formed as pouches that enclose the anode pellets 46 and 48. In particular, separator 78 is sealed at a flap 78A of material that extends around the majority of the perimeter of anode pellet 46 except in a beveled region 82 proximate to feedthrough wire 62 and embedded wires 64A and 64B. In like manner, separator pouch 80 is sealed at a flap 80A of material that extends around the majority of the perimeter of anode pellet 48 except in a beveled region 84 thereof. The individual sheets of separator material are closed at flaps 78A and 80A by a process such as ultrasonic welding, or heat sealing.

The separators 78 and 80 prevent an internal electrical short circuit between the anode and cathode active materials in the assembled capacitor and have a degree of porosity sufficient to allow flow therethrough of the working electrolyte during the electrochemical reaction of the capacitor 10. Illustrative separator materials include woven and non-woven fabrics of polyolefinic fibers including polypropylene and polyethylene, or fluoropolymeric fibers including polyvinylidene fluoride, polyethylenetetrafluoroethylene, and polyethylenechloro-trifluoroethylene laminated or superposed with a polyolefinic or fluoropolymeric microporous film, non-woven glass, glass fiber materials and ceramic materials.

Suitable microporous films include a polyethylene membrane commercially available under the designation SOLUPOR®, (DMS Solutech); a polytetrafluoroethylene membrane commercially available under the designation ZITEX®, (Chemplast Inc.) or EXCELLERATOR®, (W. L. Gore and Associates); a polypropylene membrane commercially available under the designation CELGARD®, (Celgard LLC); and a membrane commercially available under the designation DEXIGLAS®, (C. H. Dexter, Div., Dexter Corp.). Cellulose based separators also typically used in capacitors are contemplated by the scope of the present invention. Depending on the electrolyte used, the separator can be treated to improve its wettability, for example with a surfactant, as is well known by those skilled in the art.

The structure of the cathode is best understood with reference to FIGS. 5 to 9. Referring first to FIG. 9, portions of a cathode active material 90 contact the inner surfaces of the casing face walls 18 and 24. Another portion of the cathode active material 90 is positioned intermediate the anodes 46 and 48. The cathode active material 90 intermediate the anodes 46 and 48 is supported on the opposed surfaces 92 and 94 of a current collector 96 (FIG. 5), preferably in the form of a foil.

The cathode active material 90 has a thickness of about a few hundred Angstroms to about 0.1 millimeters directly coated on the inner surface of the face walls 18 and 24 of casing members 14 and 16, or it may be coated on a conductive substrate (not shown) in electrical contact with the inner surface of the face walls. In that respect, the face walls 14 and 16 and the current collector 96 may be of an anodized-etched conductive material, or have a sintered active material with or without oxide contacted thereto, or be contacted with a double layer capacitive material, for example a finely divided carbonaceous material such as graphite or carbon or platinum black, or be contacted with a redox, pseudocapacitive or an under potential material, or an electroactive conducting polymer such as polyaniline, polypyrrole, polythiophene, and polyacetylene, and mixtures thereof.

According to one preferred aspect of the present invention, the redox or cathode active material includes an oxide of a first metal, the nitride of the first metal, the carbon nitride of the first metal, and/or the carbide of the first metal, the oxide, nitride, carbon nitride and carbide having pseudocapacitive properties. The first metal is preferably selected from the group consisting of ruthenium, cobalt, manganese, molybdenum, tungsten, tantalum, iron, niobium, iridium, titanium, zirconium, hafnium, rhodium, vanadium, osmium, palladium, platinum, nickel, and lead.

The cathode active material 90 may also include a second or more metals. The second metal is in the form of an oxide, a nitride, a carbon nitride or carbide, and is not essential to the intended use of the conductive face walls 14 and 16 and the intermediate current collector 96 as a capacitor electrode, and the like. The second metal is different than the first metal and is selected from one or more of the group consisting of tantalum, titanium, nickel, iridium, platinum, palladium, gold, silver, cobalt, molybdenum, ruthenium, manganese, tungsten, iron, zirconium, hafnium, rhodium, vanadium, osmium, and niobium. In a preferred embodiment of the invention, the cathode active material includes an oxide of ruthenium or oxides of ruthenium and tantalum.

The mating casing members 14 and 16, and the electrically connected conductive substrate if it is provided, are preferably selected from the group consisting of tantalum, titanium, nickel, molybdenum, niobium, cobalt, stainless steel, tungsten, platinum, palladium, gold, silver, copper, chromium, vanadium, aluminum, zirconium, hafnium, zinc, iron, and mixtures and alloys thereof. Preferably, the face and side walls of the casing members 14 and 16 and the current collector 96 have a thickness of about 0.001 to about 2 millimeters.

The exemplary electrolytic-type capacitor 10 shown in FIGS. 1 and 9 has the cathode active material preferably coating the face walls 18 and 24, with the coating spaced from the side wall 20 of casing member 14 and the peripheral edge of casing member 16. Such a coating is accomplished by providing the conductive face walls 18 and 24 of the respective casing members 14, 16 with a masking material in a known manner so that only the intended area of the face walls is contacted with active material. The masking material is removed from the face walls prior to capacitor fabrication. Preferably, the cathode active material is substantially aligned in a face-to-face relationship with the major faces of the anodes 46 and 48.

A preferred coating process is by pad printing, as disclosed in U.S. Pat. No. 7,116,547 to Seitz et al. This patent is assigned to the assignee of the present invention and incorporated herein by reference. An ultrasonically generated aerosol as described in U.S. Pat. Nos. 5,894,403, 5,920,455, 6,224,985, and 6,468,605, all to Shah et al., is also suitable for making a coating of the active materials. These patents are assigned to the assignee of the present invention and incorporated herein by reference. In that manner, the ultrasonically generated active material contacted to the conductive surfaces has a majority of its particles with diameters of less than about 10 microns. This provides an internal surface area for the active material of about 10 $m^2$/gram to about 1,500 $m^2$/gram.

Figure 5:
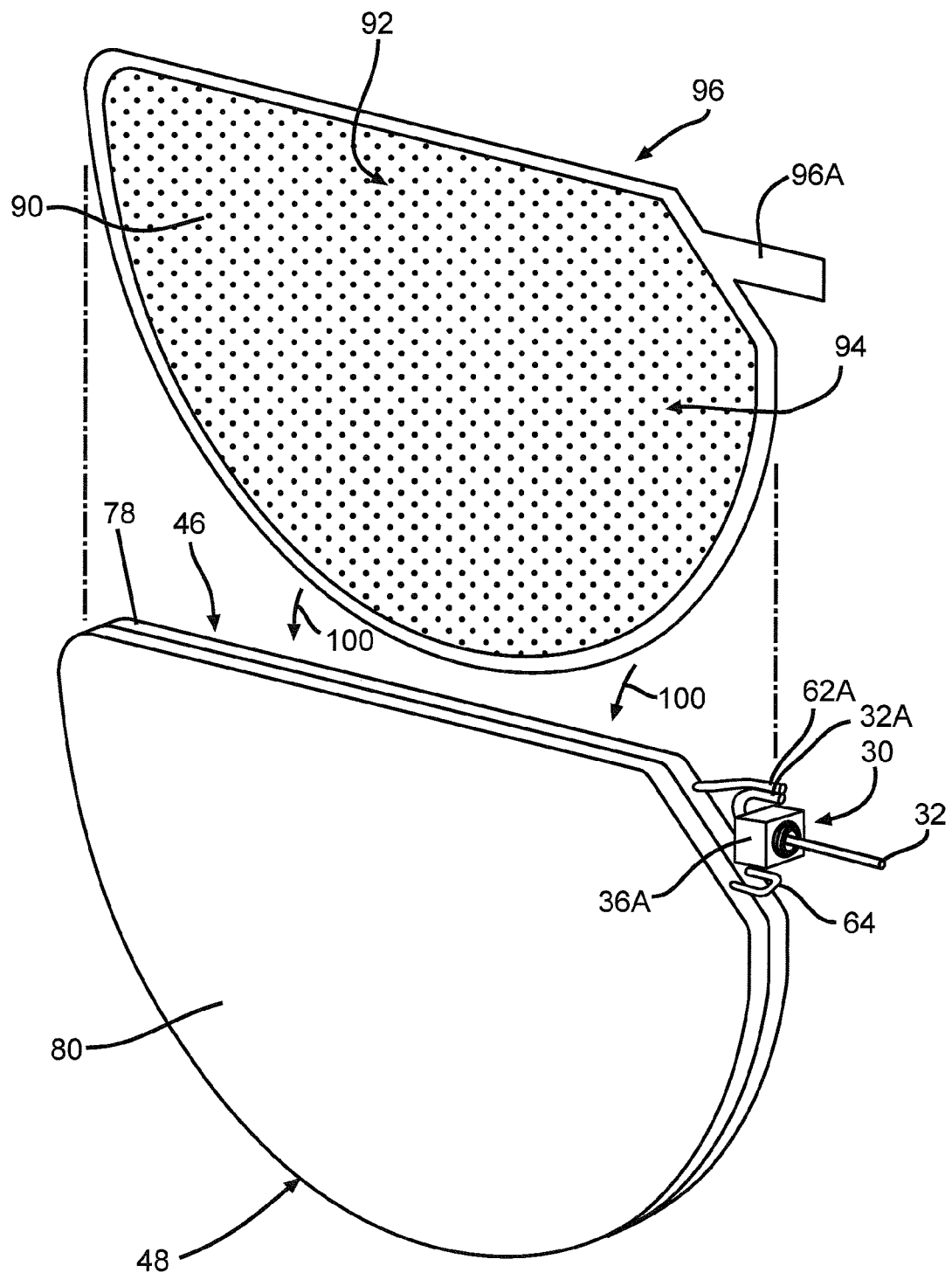
FIG. 5 is a perspective view of the dual anode assembly 60 shown in FIG. 4 with a current collector 96 supporting cathode active material 90 on its major sides being fitted between the anode pellets 46 and 48.

As shown in FIG. 5, anodes 46 and 48 are sufficiently separable due to the flexibility of the bridging wire 64 extending between the anode pellets 46, 48 to allow the current collector 96 to be inserted between them, as indicated by arrows 100. That way, the cathode current collector 96 having opposed first and second major faces 92 and 94 provided with cathode active material 90 thereon is positioned opposite the first and second anodes 46 and 48, thereby forming an anode/cathode assembly.

Figure 6:
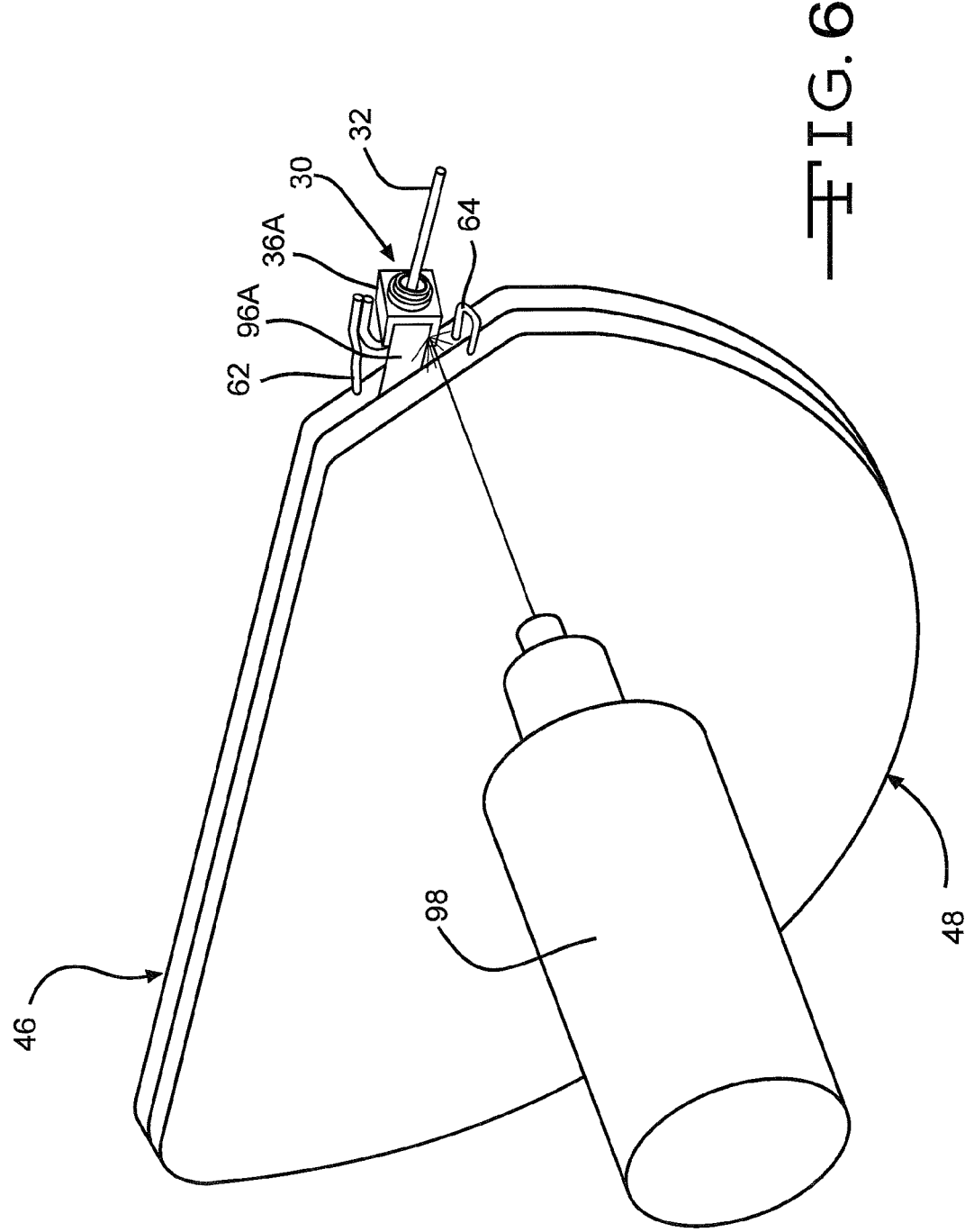
FIG. 6 is a perspective view of the dual anode/cathode assembly shown in FIG. 5 with a tab 96A of the cathode current collector 96 being welded to a ferrule 36 of the glass-to-metal seal 30.

The cathode current collector 96 comprises a tab 96A extending outwardly therefrom. The tab 96A is not provided with active material. Instead, it is left uncovered. This tab 96A is directly connected to a planar face comprising the proximal portion 36A of the previously described ferrule 36 (FIG. 2). This is preferably done using a laser 98 (FIG. 6).

Figure 6A:
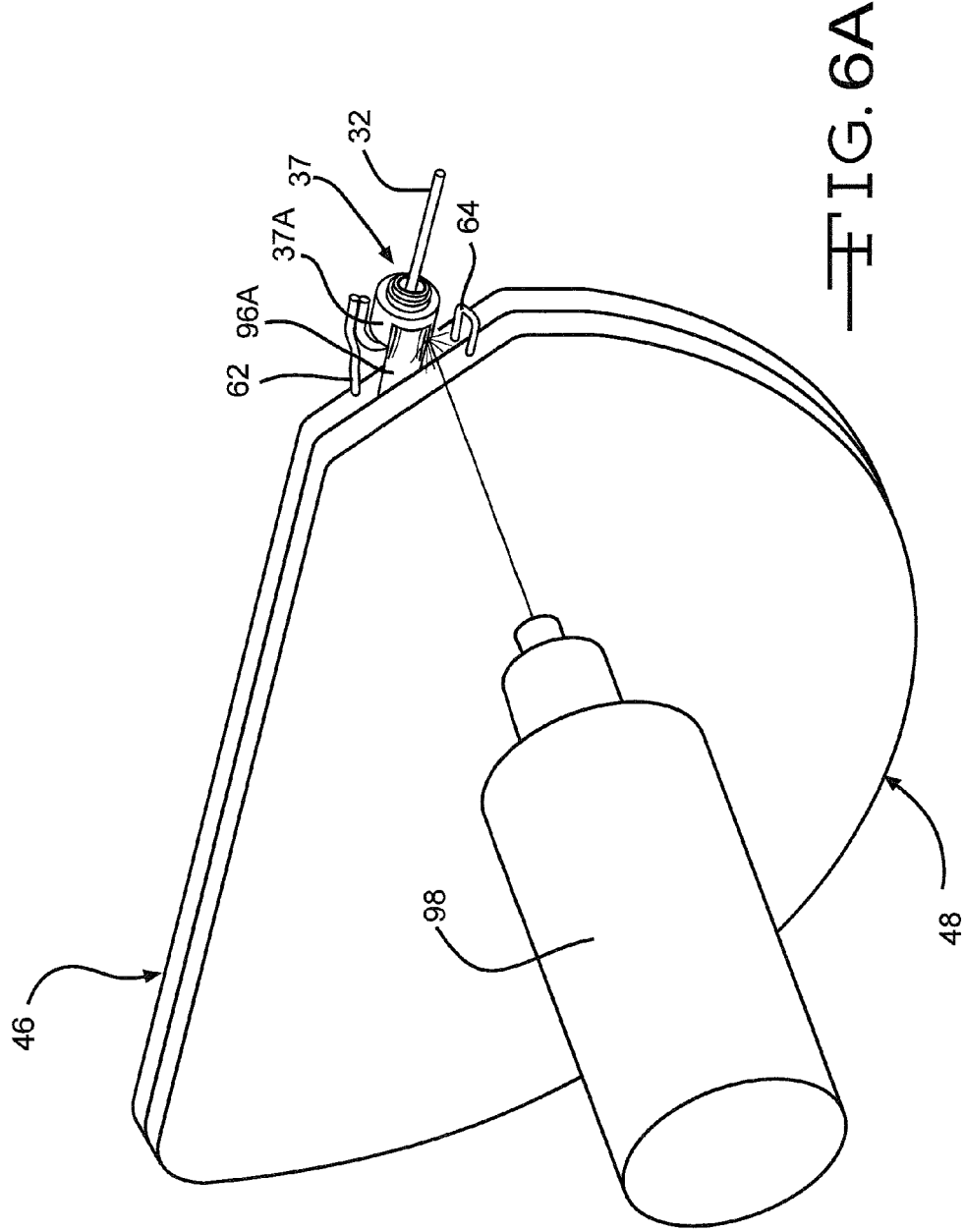
FIG. 6A is a broken away perspective view of the dual anode/cathode assembly shown in FIG. 5 with the cathode current collector tab 96A being welded to a cylindrical ferrule 37A of a glass-to-metal seal 37.

FIG. 6A is a broken away view of the cathode current collector tab 96A after having been connected to a feedthrough 37 comprising a cylindrically shaped ferrule 37A. While it is preferred to contact the tab 96A to a planar portion of a ferrule, the present invention should not be so limited. In a broader sense, the current collector tab 96A only needs to be in direct electrical continuity with the feedthrough ferrule, regardless of its shape.

Figure 7:
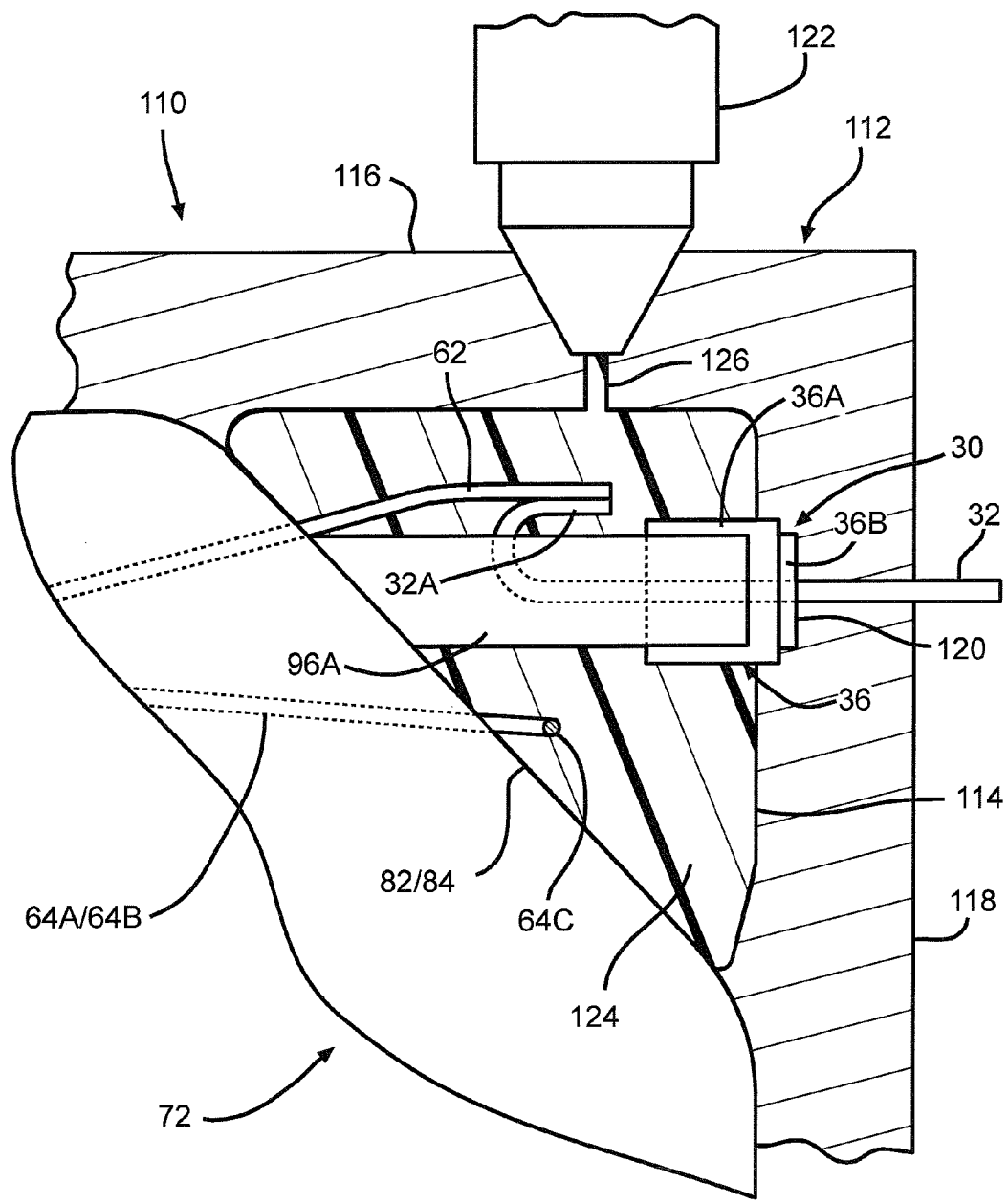
FIG. 7 is a perspective view of the anode/cathode assembly shown in FIG. 6 after injection of the polymeric material 124 to stabilize the ferrule 36 and various wires associated with the anode pellets 46, 48.
Figure 8:
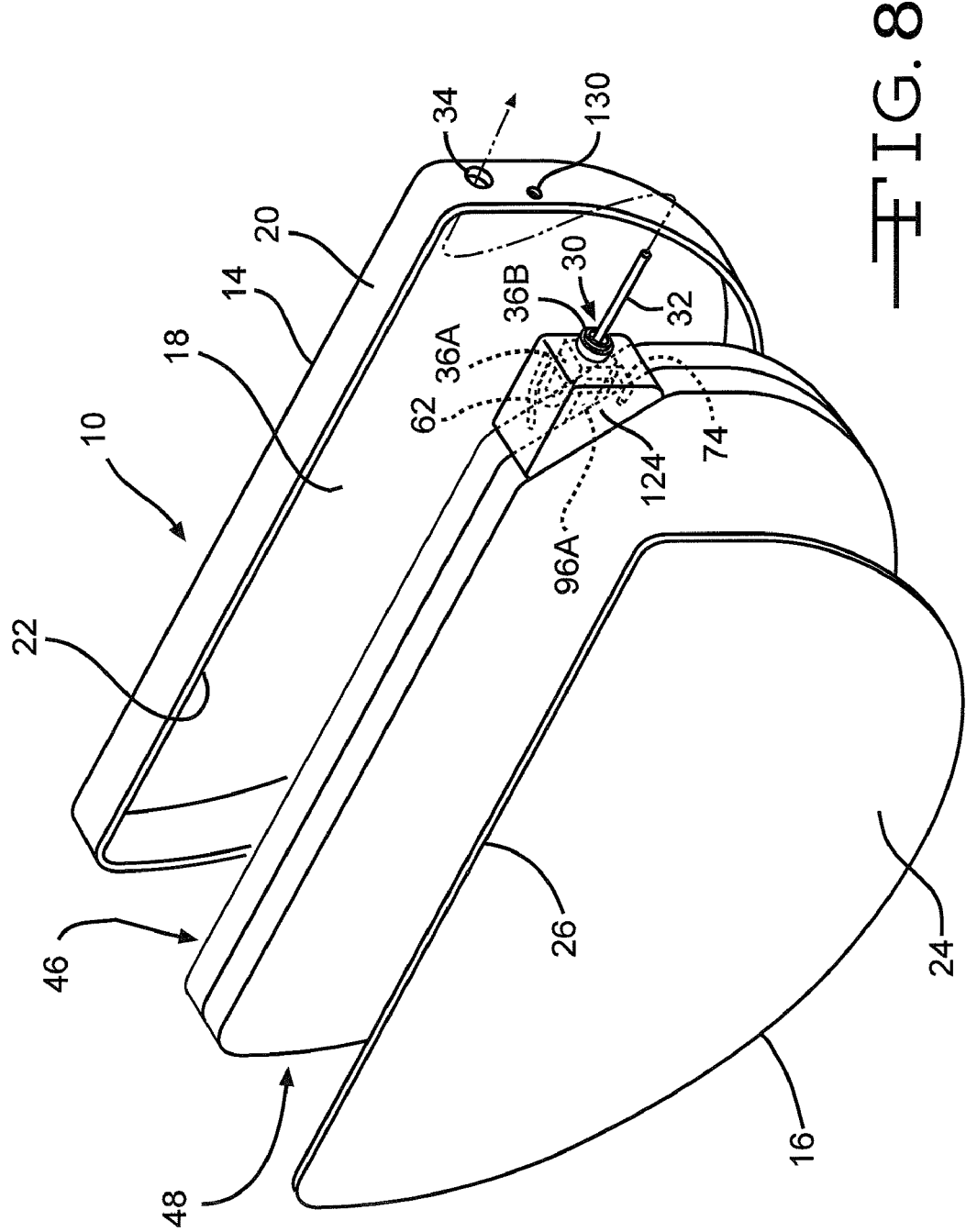
FIG. 8 is a perspective view of the anode/cathode assembly shown in FIG. 7 being fitted into one of the casing members 14.

Preferably, an additional step is performed in which the proximal portion 36A of the ferrule 36 for the GTMS, the wire 64 bridging between the anode pellets 46, 48 and the anode wire 72 connected to the terminal wire 32 are encased in a molded polymeric material. As shown in FIG. 7, this is done by positioning the anode/cathode assembly in a mold 110. A corner region 112 of the mold forms a triangular shaped hollow cavity 114 bounded by mold walls 116 and 118 and the beveled regions 82, 84 of anode pellets 46 and 48. The mold wall 118 is provided with a stepped cylindrical recess 120 that accepts the distal portion 36B of the feedthrough ferrule 36 so that this end is not potted in the injected polymer.

After the anode/cathode assembly is fitted within mold 110, a nozzle or extrusion slot die 122 is hooked up thereto. The nozzle 122 is used to inject a polymer material 124 through port or slot 126 into the hollow cavity 114. If desired, there can be more than one nozzle positioned to inject polymer 124 into the cavity. The polymeric material 124 is preferably of a fast curing type including a polyolefin, a fluoropolymer, a hot melt adhesive, or a UV curable adhesive. A relatively slow curing silastic material is also useful. This forms a polymeric mass (FIGS. 8 and 9) around the bridging wire 64 including its intermediate portion 64C, the proximal portion 36A of the feedthrough ferrule including the interior portion 32 of the terminal wire 32 and the anode wire 62, thereby enclosing and immobilizing these components.

Referring again to FIG. 8, when fabrication of the anode/cathode assembly is complete, it is positioned inside the first casing member 14. The exposed distal portion 36B of the feedthrough ferrule 36 is disposed in the opening 34 in side wall 20 with the distal end of terminal wire 32 extending outside the first casing member. The exposed distal portion 36B of the feedthrough ferrule 36 is welded to side wall 20 to join and seal the feedthrough 30 to the casing member 14.

Casing member 16 is then mated with casing member 14 and sealed thereto, preferably by laser welding. In one embodiment, the mating of casing members is as depicted in FIGS. 9 and 10. The outer edge 26 of casing member 16 is flush with side wall 20 at the outermost edge 22 of casing member 14, and weld 28 is formed at the interface between the edges 22 and 26. For a more detailed discussion regarding various casing constructions suitable for the present capacitor, reference is made to U.S. Pat. No. 7,012,799 to Muffoletto et al. This patent is assigned to the assignee of the present invention and incorporated herein by reference.

In a final step of providing capacitor 10, the void volume in casing 12 is filled with a working electrolyte (not shown) through a fill opening 130 (FIG. 1). This hole is then welded closed to complete the sealing process. A suitable working electrolyte for the capacitor 10 is described in U.S. Pat. No. 6,219,222 to Shah et al., which includes a mixed solvent of water and ethylene glycol having an ammonium salt dissolved therein. U.S. Pat. No. 6,687,117 to Liu and U.S. Patent Application Pub. No. 2003/0090857 describe other electrolytes for the present capacitor 10. The electrolyte of the latter publication comprises water, a water-soluble inorganic and/or organic acid and/or salt, and a water-soluble nitro-aromatic compound while the former relates to an electrolyte having de-ionized water, an organic solvent, isobutyric acid and a concentrated ammonium salt. These patents and publications are assigned to the assignee of the present invention and incorporated herein by reference.

Figure 11:
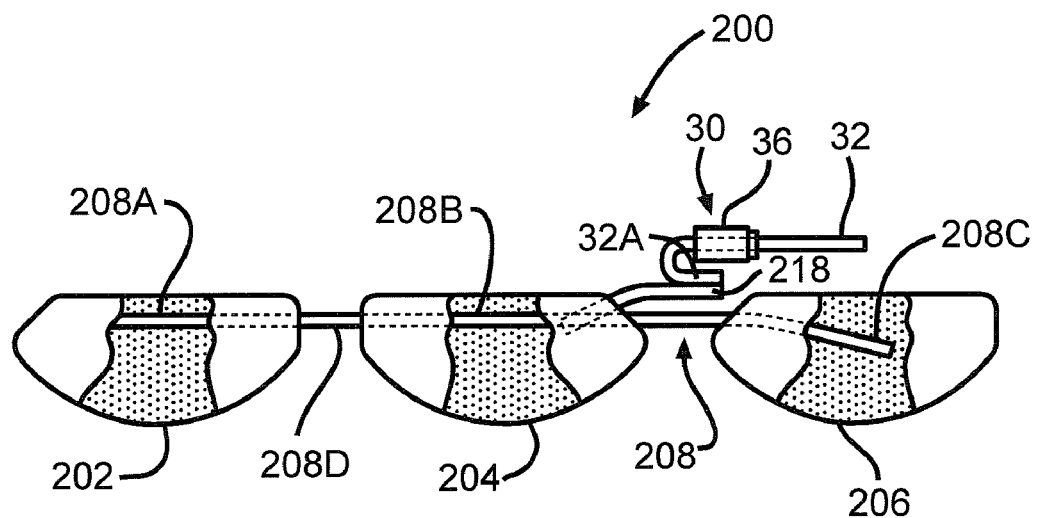
FIGS. 11 and 11A are side elevation views of anode assemblies comprising three anodes connected in series.

The capacitor of the present invention is not limited solely to a dual anode structure. For example, FIG. 11 is a side elevation view of another anode assembly 200 comprising three anodes connected in series to the terminal wire 32. Anode assembly 200 is comprised of a first anode pellet 202, a second anode pellet 204 and a third anode pellet 206. Each of the anode pellets 202, 204 and 206 is formed of active anode material and include inner and outer major face walls as described for anodes 46 and 48 of FIG. 3. An anode wire 208 extends to each of the anode pellets and comprises a first portion 208A embedded in anode pellet 202, a second portion 208B embedded in the second anode pellet 204 and a third portion 208C embedded in third anode pellet 206. An exposed portion 208D of wire 208 bridges between anode pellets 202 and 204 and an exposed portion 208E bridges between anode pellets 204 and 206. Alternatively, separate embedded anode wires can be connected to pellets 202, 204 and 206 in series.

In forming anode assembly 200 for placement in casing 12, exposed anode wire portions 208D and 208E are bent to provide the serpentine arrangement or a jellyroll arrangement of anodes 202, 204 and 206 illustrated in FIG. 12. The lengths of the intermediate bridge portions 208D and 208E between the anode pellets must be matched to the particular configuration.

Figure 11A:
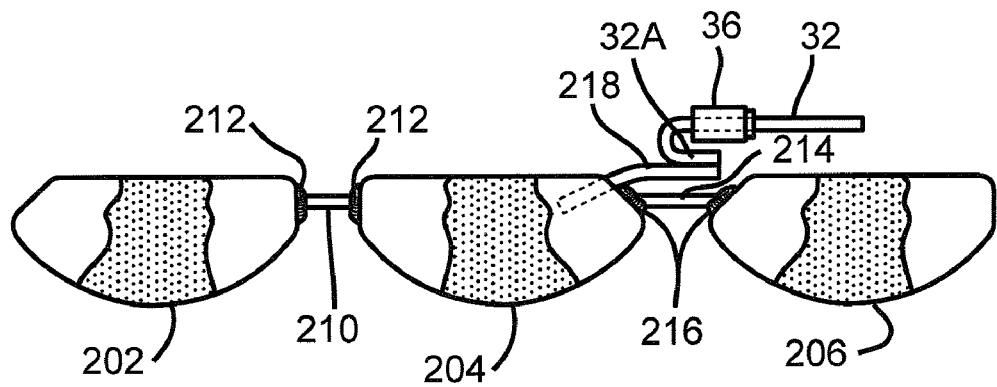

In another embodiment shown in FIG. 11A, portions of the anode wire are not embedded in the anode pellets. Instead, opposed distal ends of a wire 210 are connected to the surrounding edges of pellets 202 and 204 by welds 212 and the opposed distal ends of a wire 214 are connected to the surrounding edges of pellets 204 and 206 by welds 216.

Both anode assemblies illustrated in FIGS. 11 and 11A include a feedthrough wire 218 extending from the middle anode pellet 204. The distal end of this wire 218 is weld connected to the interior portion 32A of the terminal wire 32. Each anode pellet 202, 204 and 206 is enveloped in a separator 219.

The three anode assemblies 200 of FIGS. 11 and 11A are then folded in a manner similar to that depicted for anode assembly 44 of FIGS. 3 and 3A. The previously described first current collector 96 supporting cathode active material 90 on it major faces is positioned between anodes 202 and 204 with its tab 96A welded to one side of the GTMS ferrule 36A. A second cathode current collector 220, similar to the current collector 96, is disposed between the second and third anodes 204 and 206. The second cathode current collector has opposed first and second major faces provided with cathode active material 90 thereon. Thus, a three-anode/dual-cathode current collector assembly is provided for placement within the casing 12, as shown in FIG. 12.

In the three anode/two cathode current collector design, the tab 220A of the second cathode current collector 220 can be electrically connected to the negative polarity casing 12 in a variety of constructions. In one, the tab 220A is tack welded to a planar side of the proximal portion 36A of the feedthrough ferrule 36 opposite from the side to which the tab 96A of the first cathode current collector 96 is contacted. As discussed hereinabove, the ferrule need not have a planar surface, however, that is preferred. In alternate embodiments, the second cathode current collector tab 220A is directly connected to the casing (see the previously discussed U.S. Pat. No. 7,483,260 to Ziarniak et al.) or the first cathode current collector tab. This introduces a greater degree of flexibility to the capacitor design.

The thusly assembled anode/cathode assembly is then processed in a similar manner as previously discussed with respect to FIGS. 7 to 10 to provide a functional capacitor.

It is, therefore, apparent that there has been provided, in accordance with the present invention, a capacitor containing at least two anodes that are connected to a common terminal within the capacitor casing. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A capacitor, which comprises:
   a) a casing comprising first and second casing members secured to each other;
   b) a first anode of anode active material housed within the casing;
   c) a second anode of anode active material housed within the casing, wherein the first anode is electrically connected to the second anode by a first anode wire having opposite ends contacting the respective first and second anodes;

d) a feedthrough wire extending outside the casing and electrically isolated there from by a glass-to-metal seal, wherein the feedthrough wire is electrically connected to the first anode wire as the positive terminal for the capacitor;

e) a cathode comprising cathode active material supported by and in contact with a first face wall of the first casing member and a second face wall of the second casing member;

f) a first cathode current collector disposed between the first and second anodes and having opposed first and second major faces provided with cathode active material thereon, wherein the cathode current collector includes a tab that is physically connected to a ferrule of the glass-to-metal seal and the glass-to-metal seal is electrically connected to the casing as the negative terminal for the capacitor; and g) an electrolyte contacting the cathode and the first and second anodes.

2. The capacitor of claim 1 wherein the ferrule is sealed in an opening of one of the first and second casing members.

3. The capacitor of claim 2 wherein the tab of the cathode current collector is physically connected to a planar surface of the ferrule.

4. The capacitor of claim 2 wherein the ferrule comprises a proximal portion having a rectangular cross-section physically connected to the tab of the cathode current collector and a distal portion having a cylindrical cross-section sealed in an opening in one of the first and second casing members.

5. The capacitor of claim 1 wherein the first anode comprises a first surrounding sidewall extending to opposed first face walls and the second anode comprises a second surrounding sidewall extending to opposed second face walls and wherein the first anode wire extends to the first and second surrounding sidewalls.

6. The capacitor of claim 1 wherein the opposite ends of the first anode wire are either embedded in the respective first and second anodes or not embedded in the first and second anodes, but contacted thereto.

7. The capacitor of claim 1 wherein the feedthrough wire is connected to the first anode wire intermediate the first and second anode electrically connected in parallel.

8. The capacitor of claim 1 wherein the feedthrough wire is connected to the first anode wire extending from the first anode opposite the second anode to thereby electrically connect the first and second anodes in parallel.

9. The capacitor of claim 1 wherein the feedthrough wire is connected to a second anode wire extending from the first anode with the first and second anodes electrically connected in series.

10. The capacitor of claim 1 wherein the first casing member has a first face wall joined to a surrounding side wall and the second member has a second face wall secured to the surrounding side wall of the first casing member.

11. The capacitor of claim 1 further comprising a first separator enveloping the first anode and a second separator enveloping the second anode.

12. The capacitor of claim 1 wherein at least a portion of the first anode wire extending to the first and second anodes and at least a portion of the feedthrough wire including a portion of the glass-to-metal seal and the tab of the cathode current collector contacted thereto are enclosed in a polymeric material.

13. The capacitor of claim 1 wherein the anode active material is selected from the group consisting of tantalum, aluminum, titanium, niobium, zirconium, hafnium, tungsten, molybdenum, vanadium, silicon, germanium, and mixtures and alloys thereof, and the cathode active material is selected from the group consisting of ruthenium, cobalt, manganese, molybdenum, tungsten, tantalum, iron, niobium, iridium, titanium, zirconium, hafnium, rhodium, vanadium, osmium, palladium, platinum, nickel, lead, gold, silver, and mixtures, oxides and nitrides thereof.

14. A capacitor, which comprises:
a) a casing comprising first and second casing members secured to each other;
b) a first anode of tantalum housed within the casing;
c) a second anode of tantalum housed within the casing, wherein the first anode is electrically connected to the second anode by a first anode wire having opposite ends contacting the respective first and second anodes;
d) a feedthrough wire extending outside the casing and electrically isolated there from by a glass-to-metal seal, wherein the feedthrough wire is electrically connected to the first anode wire as the positive terminal for the capacitor;
e) a cathode comprising ruthenium oxide active material supported by and in contact with a first face wall of the first casing member and a second face wall of the second casing member;
f) a first cathode current collector disposed between the first and second anodes and having opposed first and second major faces provided with ruthenium oxide active material thereon, wherein the cathode current collector includes a tab that is physically connected to a ferrule of the glass-to-metal seal and the glass-to-metal seal is electrically connected to the casing as the negative terminal for the capacitor; and
g) an electrolyte contacting the cathode and the first and second anodes.

15. A method for providing a capacitor, comprising the steps of:
a) providing a casing comprising a first casing member and a second casing member, each of the casing members including a face wall supporting and in contact with cathode active material;
b) providing a first anode of anode active material comprising inner and outer face walls and a second anode of anode active material comprising inner and outer face walls;
c) electrically connecting the first anode to the second anode by a first anode wire having opposed ends contacting the respective first and second anodes;
d) connecting a feedthrough wire to the first anode wire as the positive terminal for the capacitor with the feedthrough wire extending outside the casing and electrically isolated there from by a glass-to-metal seal;
e) disposing a current collector having opposed first and second major faces provided with cathode active material between the first and second anodes, thereby forming an anode/cathode assembly, wherein the cathode current collector includes a tab that is physically connected to a ferrule of the glass-to-metal seal and the glass-to-metal seal is electrically connected to the casing as the negative terminal for the capacitor;
f) positioning the anode/cathode assembly inside the first casing member with the feedthrough wire extending outside the first casing member and electrically insulating there from by a glass-to-metal seal;

g) securing the first casing member to the second casing member to provide an enclosure containing the anode/cathode assembly; and h) providing an electrolyte inside the casing to operatively associate the cathode with the first and second anodes.

16. The method of claim 15 including sealing the ferrule in an opening of one of the first and second casing members.

17. The method of claim 15 including physically connecting the tab of the cathode current collector to a planar surface of the ferrule.

18. The method of claim 15 including sealing a cylindrical portion of the ferrule in an opening in a one of the first and second casing members.

19. The method of claim 15 including connecting the feedthrough wire to the first anode wire intermediate the first and second anode electrically connected in parallel.

20. The method of claim 15 including connecting the feedthrough wire to the first anode wire extending from the first anode opposite the second anode to thereby electrically connect the first and second anodes in parallel.

21. The method of claim 15 including connecting the feedthrough wire to a second anode wire extending from the first anode with the first and second anodes electrically connected in series.

* * * * *